(12) United States Patent  (10) Patent No.: US 7,081,185 B2
Matsumoto et al.  (45) Date of Patent: Jul. 25, 2006

(54) PURIFICATION APPARATUS PROVIDED WITH LOW HEAT CONDUCTIVE MEMBER

(75) Inventors: Yukihiro Matsumoto, Kobe (JP); Takeshi Nishimura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 152 days.

(21) Appl. No.: 10/254,807

(22) Filed: Sep. 26, 2002

(65) Prior Publication Data

US 2003/0062253 A1 Apr. 3, 2003

(30) Foreign Application Priority Data

Sep. 28, 2001 (JP) .............................. 2001-304051

(51) Int. Cl.
*B01D 3/00* (2006.01)
*C07C 51/44* (2006.01)

(52) U.S. Cl. ................... 202/163; 202/266; 202/267.1; 203/8; 203/DIG. 21; 562/600

(58) Field of Classification Search ................ 203/100, 203/8, DIG. 21; 202/158, 266, 163, 239, 202/267.1; 261/114.1, 114.4, 114.5; 562/600; 196/137, 119

See application file for complete search history.

(56) References Cited

U.S. PATENT DOCUMENTS

| 112,233 | A | * | 2/1871 | Fagan |
| 3,393,133 | A | * | 7/1968 | Baird ........................... 203/89 |
| 3,988,213 | A |   | 10/1976 | Yoshida et al. |
| 4,028,443 | A | * | 6/1977 | Livingston et al. ......... 202/158 |
| 4,050,609 | A | * | 9/1977 | Okamoto et al. ...... 220/560.09 |
| 4,282,058 | A | * | 8/1981 | Gruter et al. .............. 159/13.1 |
| 4,331,127 | A | * | 5/1982 | Grosso .................... 126/378.1 |
| 4,369,097 | A |   | 1/1983 | Nezu et al. |
| 6,214,174 | B1 | * | 4/2001 | Matsumoto et al. ........ 202/266 |
| 6,409,886 | B1 | * | 6/2002 | Matsumoto et al. ........... 203/8 |

FOREIGN PATENT DOCUMENTS

JP 63-11921 3/1988

* cited by examiner

*Primary Examiner*—Virginia Manoharan
(74) *Attorney, Agent, or Firm*—Wenderoth, Lind & Ponack, L.L.P.

(57) ABSTRACT

The object of this invention to provide an improved arrangement that enables to prevent adhesion of polymer on or around the inner wall of a purification apparatus directly equipped on the outer wall thereof with an attachment such as a support by suppressing local temperature lowering inside the apparatus due to the existence of the attachment. The present invention provides a purification apparatus comprising an attachment directly mounted on an outer wall of the apparatus; and a covering material made of a low heat conductive material which partly or entirely covers the outer wall of the apparatus, and which partly or entirely covers the attachment.

16 Claims, 3 Drawing Sheets

PURIFICATION APPARATUS PROVIDED WITH LOW HEAT CONDUCTIVE MEMBER

BACKGROUND OF THE INVENTION

1. Field of the Invention

This invention relates to a technology of suppressing lowering of a temperature inside a purification apparatus due to a temperature difference between the apparatus-interior temperature and an apparatus-exterior temperature, and more particularly to a technology of suppressing polymerization of easily-polymerizable compounds on or around an inner wall of the purification apparatus.

2. Description of the Related Art

Vinyl compounds such as (meth)acrylic acid are known as easily polymerizable compounds. Particularly, in a purification process of (meth)acrylic acid and its ester in a purification apparatus such as a distillation column, such a compound is easily polymerized in the purification apparatus. Therefore, it is required to suspend the operation of the purification apparatus periodically to remove polymerized compounds.

One of the known techniques to prevent polymerization of easily-polymerizable compounds in the purification apparatus is to add a polymerization inhibitor such as hydroquinone to the purification apparatus. Another known technique to suppress adhesion of polymer on or around the inner wall of the apparatus is to apply a surface treatment that enhances smoothness on the inner wall of the apparatus such as disclosed in Japanese Patent No. 2633277.

Use of the polymerization inhibitor, however, cannot securely prevent polymerization in a condition in which (meth)acrylic acid is extremely likely to polymerize. For instance, in a case where a (meth)acrylic acid aqueous solution is subjected to distillation in an azeotropic distillation column (column for separating water component and crude (meth)acrylic acid), (meth)acrylic acid easily polymerizes in the azeotropic distillation column despite the use of a polymerization inhibitor. As the polymerization progresses, the distillation efficiency in the distillation column is gradually lowered, which necessitates suspending operation of the purification apparatus including the azeotropic distillation column to remove the polymer. Theoretically, it is possible to improve or at least secure a certain polymerization preventive effect by increasing the amount of a polymerization inhibitor to be added to the purification apparatus. However, such an attempt of preventing or suppressing polymerization has a limitation. In addition to this, gas in the distillation column does not contain a polymerization inhibitor, but rather contains an easily-polymerizable compound. Therefore, polymers unavoidably generate on or around the inner wall of the distillation column in contact with such an easily-polymerizable-compound-containing gas (hereinafter, the area of the inner wall in contact with the gas is sometimes referred to as "gas-phase contact area").

Japanese Examined Patent Publication No. 63-11921 discloses a method of preventing polymerization of a condensate even in a condition in which substantially no polymerization inhibitor exists in the distillation column. In this method, a heating means (e.g., heating jacket) is mounted or covered over the distillation column to prevent condensation of vapors on or around the gas-phase contact area of the column, thus preventing polymerization of the condensate. This method requires heating the purification apparatus from the outside. This method is infeasible particularly in a case of mounting a heating jacket over a large-scaled distillation column because the facility cost is expensive, and the temperature control inside the distillation column is difficult.

There has also been proposed an idea of providing a heating means such as a heating jacket on the outer wall of the distillation column and passing a heating medium such as warm water, hot water, and steam inside the heating jacket to prevent condensation of the easily-polymerizable-compound-containing gas on or around the gas-phase contact area of the column so as to suppress generation of polymer on or around the gas-phase contact area. However, the idea of providing a heating jacket in the above manner involves a drawback in that excessive heating leads to unstable running of the distillation column. Further, the above idea is not desirable with respect to safety measures because once the heating jacket causes breakage or damage, the heating medium running in the heating jacket is likely to flow or come outside. Particularly, the idea of passing a heating medium inside a heating jacket may encounter the following difficulty. When the above technology of providing a heating jacket and passing a heating medium inside the heating jacket is applied to the distillation column equipped with an attachment, the heating jacket is required to be mounted over the distillation column in such a manner as to avoid the region where the attachment is mounted because of the fact that passing the heating medium inside the heating jacket mounted over the outer wall of the distillation column including the attachment mounted region hinders efficient heating of the column outer wall. Therefore, in case of mounting a heating jacket over the distillation column directly equipped with an attachment on the outer wall thereof, the installed location of the heating jacket is restricted by the existence of the attachment to a location where an attachment is less likely to be mounted, such as an upper part or a lower part of the distillation column. The restricted installation of the heating jacket cannot sufficiently prevent generation of a polymer on or around the gas-phase contact area and/or adhesion of such polymer thereto. In such an arrangement, it is highly likely that a polymer will generate and/or adhere on or around the inner wall region (gas-phase contact area) of the column corresponding to the site where the heating jacket is not mounted.

Liquids and gases are fed in and out of the distillation column through pipes. Specifically, taking an example of a liquid, the liquid is fed out of the distillation column and is drawn into a reboiler where the liquid is heated, and the heated liquid is fed back to the distillation column. At the time of circulating the liquid through a reflux pipe from the reboiler to the distillation column, there is a possibility that the liquid temperature may be lowered in the course of circulating. Heat insulating means such as a heating jacket is covered over the circulation pipe to prevent such a temperature lowering. Similar to the heat insulating means mounted on the reflux pipe, heat insulating means such as a heating jacket and a heat insulator is mounted over a gas-phase contacting pipe which connects the reboiler and the distillation column, or over a nozzle connecting a communication port of the distillation column with a communication port of the reboiler. This arrangement is effective in suppressing polymerization of the easily-polymerizable compound contained in the gas on or around the pipe or the nozzle by preventing condensation of the gas on or around the pipe or the nozzle. However, it is not effective in preventing generation of a polymer with respect to the whole interior of the distillation column.

SUMMARY OF THE INVENTION

In view of the above, it is an object of the present invention to overcome the problems residing in the prior art. It is another object of this invention to provide an improved arrangement that prevents adhesion of a polymer on or around the inner wall (inner surface) of a purification apparatus directly equipped on the outer wall (outer surface) thereof with an attachment such as a support, by suppressing local temperature lowering inside the apparatus due to the existence of the attachment. It is yet another object of this invention to provide a technology of efficiently suppressing adhesion of polymer particularly on the apparatus inner wall corresponding to a site where the attachment is mounted.

Accordingly, the invention provides a purification apparatus comprising: an attachment directly mounted on an outer wall of the apparatus; and a covering material made of a low heat conductive material which partly or entirely covers the outer wall of the apparatus, and which partly or entirely covers the attachment.

These and other objects, features and advantages of the present invention will become more apparent upon a reading of the following detailed description and accompanying drawings.

DETAILED DESCRIPTION OF THE PREFERRED EMBODIMENTS OF THE INVENTION

Figure 1:
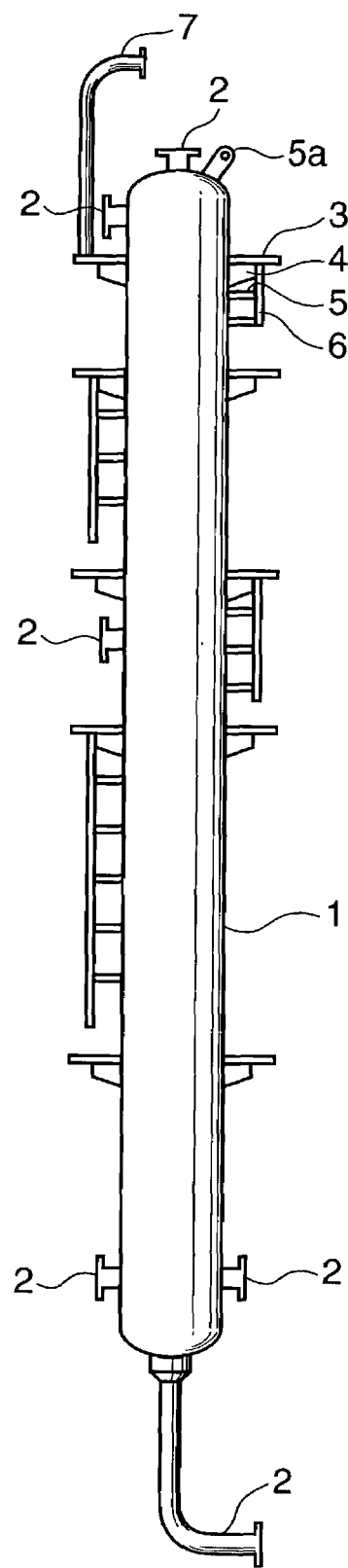
FIG. 1 is an elevational view of a purification apparatus directly mounted with an attachment on an outer wall thereof according to an embodiment of this invention.

As a result of an extensive study and research concerning suppressing generation and adhesion of polymer on or around an inner wall of a purification apparatus, particularly, on or around a gas-phase contact area of the inner wall of the purification apparatus, the present inventors found an effective arrangement of suppressing generation and adhesion of a polymer on the apparatus inner wall (inner surface) without providing a heating means such as a heating jacket for heating the interior of the apparatus from outside of the apparatus in a condition in which the interior temperature of the apparatus is higher than the exterior temperature of the apparatus. In particular, they found that, in a purification apparatus of industrial use for use in conducting a process of producing (meth)acrylic acid and its ester which is directly mounted with an attachment on the outer wall thereof, reducing heat dissipation caused by the provision of the attachment is remarkably effective in suppressing generation and adhesion of a polymer on the gas-phase contact area of the apparatus inner wall.

According to an aspect of this invention, a part or the entirety of the outer wall (outer surface) of the apparatus is covered with a covering material made of a low heat conductive material (hereinafter sometimes called "low heat conductive material"), and also a part or the entirety of an attachment mounted on the apparatus outer wall is covered with such a low heat conductive material.

In the case where a mounted member such as a lug is mounted on an attachment such as a support member which is directly mounted on the apparatus outer wall, it is recommended to provide a low heat conductive member in such a manner that the low heat conductive member is provided between the attachment and the mounted member, in combination with the arrangement in which at least part of the outer surface of the mounted member and the outer surface of the attachment including a connected portion connecting the attachment and the mounted member with the low heat conductive member interposed therebetween) is covered with the low heat conductive material to improve the heat dissipation suppression effect.

Hereinafter, this invention is described in detail with reference to a purification apparatus exemplified in FIGS. 1 through 3. It should be appreciated that this invention is not restricted by the illustrated examples.

Throughout the description of this invention, the term "purification apparatus" refers to an apparatus or a device used in purification of a substance, specifically, for heating an admixture containing at least two kinds of liquids whose boiling points are different from each other to vaporize the admixture, and for condensing the resultant vapors primarily containing the low-boiling-point component to separate the components of the admixture. This invention is applicable, in addition to the apparatus designed for purification, to an apparatus used in various distillations such as vacuum distillation (reduced-pressure distillation), azeotropic distillation, extractive distillation, stripping, absorption, and flash vaporization. Some of the exemplified purification apparatuses are a distillation column, a stripping column, an absorption column, a flash drum, and an agitation tank.

Substances to be purified are not specifically limited. Preferably, easily-polymerizable compounds which are likely to cause generation and adhesion of a polymer on the inner wall of the purification apparatus are used as compounds or substances to be purified so as to utilize the effects of this invention optimally.

Throughout the description of this invention, "easily-polymerizable compound" refers to a compound that is easy to polymerize in the purification apparatus. Exemplified easily-polymerizable compounds that are likely to polymerize in the purification apparatus during production of (meth) acrylic acid and its ester are (meth)acrylic acid, methylester, ethylester, n-propylester, isopropylester, n-butylester, isobutylester, 2-ethylhexylester, 2-hydroxyethylester, and N-N-dimethylamino ethylester.

A distillation column 1 in FIG. 1 is an example of a vessel of the purification apparatus. The installed internals in the purification apparatus are optionally selected depending on the distillation method and the substance to be distillated. For instance, a dualflow tray, a sieve tray, a valve cap tray, and packing such as cascade mini-ring, mellapak, or sulzerBX are provided in the purification apparatus according to needs.

Some of the examples of the attachment directly equipped on the outer wall of the purification apparatus are a condenser support (not shown), a platform support 4, a ladder support 14, a lifting lug 5$a$, and a davit 7. The attachment is not restricted by the aforementioned examples. Throughout the description of this invention, the term "directly" or "direct" indicates that an attachment (e.g., platform support 4 in FIG. 2) is directly attached to the apparatus outer wall by welding or its equivalent. The number and the configuration of the attachments are not restricted by the arrangement shown in the drawings, and are optimally set according to needs.

Throughout the description of this invention, the term "mounted member" means a member which is mounted on the attachment that is directly attached to the apparatus outer wall. Thus, the mounted member is indirectly mounted on the apparatus outer wall, such as a platform 3, a ladder 6 and lug 5.

The outer wall of the purification apparatus 1 is not restricted to a specific type, as long as it is made of a material having a certain pressure resistance, corrosion resistance, durability and strength to cope with the required operating conditions such as temperature. Preferably, the apparatus outer wall is made of a stainless steel excellent in pressure resistance, corrosion resistance, strength, etc.

The platform 3 is a floor for use in maintenance of the apparatus. The platform is, for example, a flat plate-like member such as an iron plate. The platform support 4 is a support member for supporting the platform 3 in association with the lug 5, as shown in FIG. 2. The ladder support 14 is a support member for supporting the ladder 6 in association with the lug 5 as shown in FIG. 3. The configuration and the material, etc. of the attachment and the mounted member such as the platform support 4, the ladder support 14 and lug 5 are not restricted to the examples shown in the embodiment. The davit 7 is a lifting component for lifting a tray, a packing, etc. above the ground to a predetermined position on the distillation column 1. The lifting lug 5a is a lifting component for raising a purification apparatus such as a distillation column in an upright posture. The davit 7 and the lifting lug 5a are generally attached to an upper part of the purification apparatus depending on their necessity. The lug 5 is a mounting tool for supportively mounting a ladder, a platform, etc. on the outer wall of the purification apparatus. The support structure of the purification apparatus is not restricted to the example shown in the drawings. Any type of structure such as skirt-structure, supporting-legged-structure, or lug-structure can be applied.

The low heat conductive material composing the covering material is a material having low heat conductivity to prevent heat dissipation and absorption. The covering material made of the low heat conductive material is adapted to cover the outer surface of the apparatus main body, the attachment, and the mounted member. Any kind of material having the above properties is usable as the low heat conductive material. Examples of the low heat conductive material are rock wool heat insulating material (JIS A 9504), glass wool heat insulating material (JIS A 9505), heat insulating material containing potassium silicate (JIS A 9510), heat insulating material containing water-repellent perlite (JIS A 9512), and heat insulating material of hard polyurethane foam (JIS A 9514). It is needless to say that the known heat insulating materials and heat blocking materials (non-heat-conductive material) can be used as a low heat conductive material. It is recommended, however, to use a low heat conductive material having heat conductivity of 0.15 W/m·K or less to effectively prevent heat escape.

In this embodiment, different kinds of low heat conductive materials can be used for the covering material depending on the mounted site of the covering material. Further, the covering material may be a multi-layer each composed of a different material to improve durability or apply weather-proof, waterproof or the like to the apparatus depending on the purpose of use.

The method of covering the attachment as well as the outer surface of the distillation tower and the mounted member with the low heat conductive material is not restricted, and any known method is applicable. It is desirable, however, to provide a heat insulator fixing member, so that the low heat conductive material may not be displaced to the attachment after mounting the attachment mounted with the low heat conductive material onto the purification apparatus.

Figure 2:
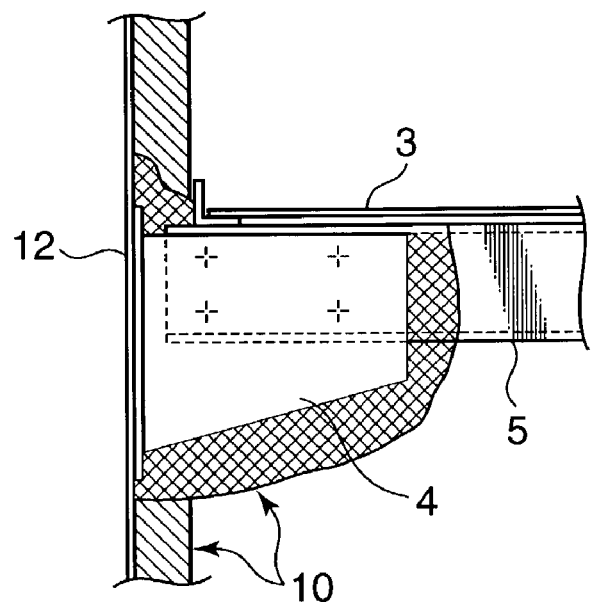
FIG. 2 is a sectional view showing an example as to how a low heat conductive member covers the attachment.
Figure 3:
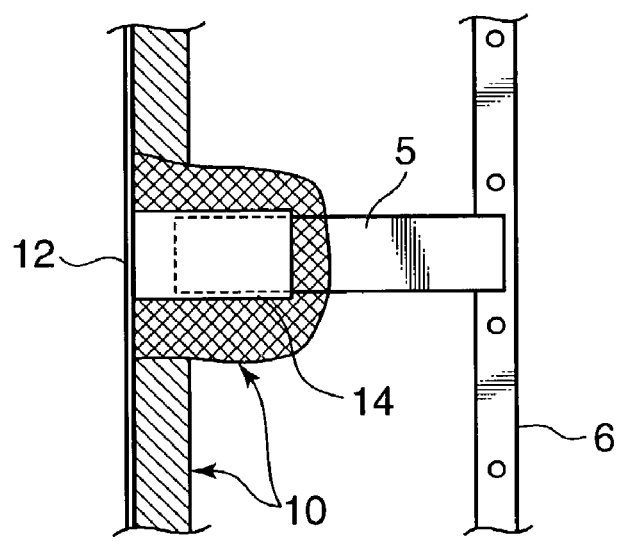
FIG. 3 is a sectional view showing another example as to how the low heat conductive member covers the attachment.

FIGS. 2 and 3 are sectional views showing an example of covering the attachment with the low heat conductive material. In FIGS. 2 and 3, the left side corresponds to the inner side of the apparatus, and the right side corresponds to the outer side of the apparatus.

In FIG. 2, the platform support 4 is directly mounted on an outer wall 12 of the distillation column 1. The platform 3 is supported on the platform support 4 by way of the lug 5, and thus is indirectly mounted on the outer wall 12. Numeral 10 denotes the low heat conductive member. The hatched portion indicates a portion of the low heat conductive member 10 which covers the apparatus outer wall 12, and the mesh portion indicates a portion of the low heat conductive member 10 which covers the attachment (in this case, platform support 4).

It is preferable to provide the low heat conductive member between the lug 5 and the platform support 4 and/or between platform 3 and the upper surface of the platform support 4 and lug 5 which is brought into contact with the platform 3 to suppress heat dissipation through the lug 5 and the platform 3 where the low heat conductive material 10 is not mounted. Namely, covering the outer surface of the attachment such as the platform support 4 with the low heat conductive material 10 in combination with placing the low heat conductive member between the attachment such as the platform support 4 and the mounted member such as lug 5 provides improved heat dissipation suppression effects. In the arrangement of FIG. 2, it is possible to provide an external heating means such as a heating jacket in place of the low heat conductive member 10 shown by the hatched portion.

Providing the above heat dissipation suppression arrangement is effective in suppressing generation and adhesion of the polymer on or around the apparatus inner wall in producing (meth)acrylic acid and its ester in the case where the interior temperature of the apparatus is higher than the exterior temperature of the apparatus. Particularly, this arrangement is effective in suppressing generation of a polymer in a condensate, as a result of condensation of vapors under the condition that substantially no polymerization inhibitor is contained in the vapors. In view of the above drawback, it is recommended to prevent heat dissipation by entirely or partially covering the apparatus with the low heat conductive material 10.

As shown in FIG. 2, it is desirable to cover the outer surface of the platform support 4 with the low heat conductive material 10 as shown by the mesh portion in FIG. 2, in addition to covering the apparatus outer wall 12 with the low heat conductive material 10 as shown by the hatched portion in FIG. 2. It is desirable to cover the attachment and the entirety of the apparatus outer wall 12 with the low heat conductive material 10 for suppressing heat dissipation. However, partly covering the attachment and the apparatus outer wall 12 may also be effective in suppressing heat dissipation. FIG. 2 shows a case in which the platform 3 is not covered with the low heat conductive material 10 in view of the operability of the apparatus. Alternatively, part or all of the platform 3 may be covered with the low heat conductive material 10, and part or all of the lug 5 may be covered with the low heat conductive material 10. In case of covering part of the mounted member with the low heat conductive material 10, it is preferable to cover the part of the mounted member at a site which is most closely located to the apparatus outer wall 12 in view of suppressing heat dissipation.

Figure 4:
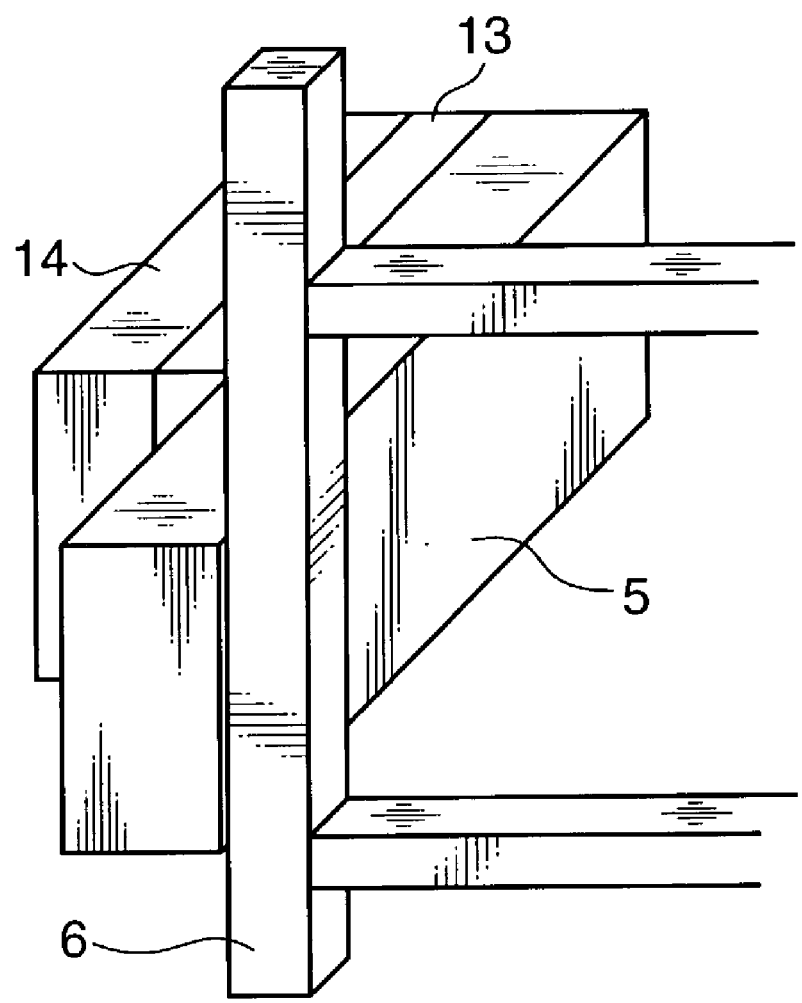
FIG. 4 is an explanatory diagram showing an example as to how the low heat conductive member is provided between the attachment and the mounted member.

FIG. 3 is a schematic diagram showing an example in which the ladder support 14 is directly mounted on the outer wall 12 of the distillation column 1. The ladder 6 is mounted on the ladder support 14 by way of the lug 5. In this case, mounting the lug 5 on the ladder support 14 in such a manner that the low heat conductive member 13 is provided between the ladder support 14 and the lug 5, as shown in FIG. 4, is effective in suppressing heat dissipation from the ladder support 14. Thus, providing the low heat conductive member 13 between the ladder support 14 and the lug 5 in combination with covering the outer surface of the ladder support 14 and part of the lug 5 which is most closely located to the outer wall 12 (see the hatched portion in FIG. 3) with the low heat conductive material 10 is desirable. Although not shown, it is possible to cover a portion of the lug 5 to be connected with the ladder 6 with the low heat conductive material 10, or to connect the ladder 6 to the lug 5 with the low heat conductive member 13 interposed therebetween. In either way, increasing the covered area of the attachment and the mounted member, which is directly or indirectly in contact with the outer wall 12 of the apparatus, by the low heat conductive material 10 is effective in suppressing heat dissipation.

Also, although not illustrated in the drawings, it is desirable to partly or entirely cover the attachment such as the lifting lug 5a and the davit 7 with the low heat conductive member 10 as with the cases of the arrangements shown in FIGS. 2 and 3. In the case of partially covering the attachment, it is recommended to mount the low heat conductive member 10 on the attachment at a site which is most closely located to the outer wall 12.

The low heat conductive member 13 is a member which is to be provided between an attachment such as the support 4 and a mounted member such as the lug 5, and which has a low heat conductivity. Exemplified members are a gasket and a sheet. As long as the member 13 is free from cracks and other defects when the attachment is mounted on the apparatus in a state such that the member 13 is provided between the attachment and the mounted member, the type and material of the member 13 is not restricted. Some of the examples of the material for the low heat conductive member 13 are ceramics, asbestos, teflon, and teflon-coated asbestos. However, as long as the material is a low heat conductive material or a non-heat conductive material, the material is not restricted to the ones shown in this embodiment.

As shown in FIGS. 2 and 3, it is desirable to cover the outer surface of the attachment and the outer surface of the mounted member including the connected portion of the attachment and the mounted member with low heat conductive material interposed therebetween for suppressing heat dissipation. In this specification, the expression "outer surface of the mounted member" indicates the surface portion which includes at least part of the outer surface of the mounted member most closely located to the connected portion. When attempting suppression of heat dissipation with respect to the entirety of the apparatus including the mounted member, such as the lug, which is indirectly mounted on the apparatus by way of the attachment, it is desirable to cover the outer surface of the mounted member such as the lug with the low heat conductive material.

It is desirable to use the inventive purification apparatus in conducting a process of producing (meth)acrylic acid. The process of producing (meth)acrylic acid is not limited to a specific one. An exemplified method comprises the steps of: conducting catalytic gas phase oxidation of propylene or the like with a molecular-oxygen-containing gas in the presence of an oxidation catalyst to yield a reaction product (acrylic acid as a target product, byproducts such as acetic acid, formic acid, acetaldehyde, formaldehyde, mixed gas containing unreacted raw material such as propylene and acrolein); drawing the reaction product to an acrylic acid collecting column for contact with water to cool the reaction product while absorbing and collecting acrylic acid so as to obtain an aqueous solution containing crude acrylic acid and a byproduct such as acetic acid; and separating and purifying the acrylic acid in the aqueous solution according to an optional distillation method using the inventive distillation column so as to obtain purified acrylic acid as an end product. Various apparatuses can be additionally provided or omitted according to the purpose of use, and a desired apparatus can be combined to execute a process of producing (meth)acrylic acid.

Hereinafter, the present invention is described based on examples. It should be appreciated that the invention is not restricted to the following examples.

EXAMPLE 1

A six-staged platform (see FIG. 2) was attached to an outer wall of a tray type distillation column (inner diameter: 1850 mm, internally provided with 50 stainless steel dual-flow tray) as shown in FIG. 1, which is a generally used distillation column for distilling (meth)acrylic acid or its ester. As shown in FIG. 3, a ladder 6 was mounted on the distillation column by way of a ladder support 14 and a lug 5, each of which was covered with the low heat conductive material 10 primarily made of calcium silicate. Further, the outer wall of the distillation column including a pipe joint 2 and a nozzle 9 for connecting the distillation column with a reboiler (not shown) were covered with the low heat conductive member 10. Furthermore, as shown in FIG. 4, a gasket 13 (product of Nippon Valqua Industries, Ltd.; Valqua 1500AC), which is a low heat conductive member, was provided between the ladder support lug 14 and the lug 5 Likewise, a gasket equivalent to the gasket 13 was provided between the platform support 4 and the lug 5. A raw material liquid such as a starting material containing 96.8 mass % of acrylic acid and 2.1 mass % of acrylic acid dimer was fed to the above-constructed distillation column, and distillation was performed for 10 consecutive days under the conditions of a column top pressure of 4.7 kPa, temperature of 63 C.°, and reflux ratio of 0.9. The acrylic acid component in the starting material was evaporated by heating in the column, and raised upward in the column. Then, after being fed to the condenser (not shown) through the top of the column, the vaporized acrylic acid component was condensed and discharged out of the column. The high-boiling-point-component such as acrylic acid dimer was fed to a next step (not shown) through the bottom of the column, and part of the bottom liquid was refluxed to the distillation column by way of the unillustrated reboiler. The condensate extracted from the condenser contains acrylic acid or the like component. In this way, part of the condensate was refluxed to the column as a reflux liquid to raise yield of (meth)acrylic acid. At the same time, part of the condensate was brought to a gas-phase contact in the distillation column, and the resultant acrylic acid or the like component was allowed to flow to the bottom of the column. Phenothiazine as a polymerization inhibitor was added to the starting material and the reflux liquid. After running the column for 10 consecutive days under the above conditions, the operation of the column was suspended. Then, the column was disassembled for checking the inside of the column. As a result of checking, no adhesion of polymer was found on the inner wall of the distillation column.

EXAMPLE 2

The Example 2 is different from the Example 1 in that a gasket was not provided between the ladder support and the lug.

The distillation column constructed as above was operated for 10 consecutive days under the same conditions as the Example 1. Upon lapse of 10 days, the column was disassembled for checking the inside of the column. As a result of checking, even though it was found that a small amount of polymer was adhered on the welded portion of the inner wall surface of the column main body which was joined with the support, an allowable polymerization suppression effect was obtained.

COMPARATIVE EXAMPLE 1

Comparative Example is similar to the Example 1 in that the outer wall of a distillation column and a nozzle to be connected to the column were covered with the low heat conductive material (see the hatched portions in FIGS. 2 and 3). The Comparative Example 1 is different from the Example 1 in that the attachments such as the platform support and the ladder support, and the mounted members such as the lug were not covered with the low heat conductive material (see the mesh portions in FIGS. 2 and 3), and a gasket was not provided between the ladder support and the lug and between the platform support and the lug. The distillation column constructed as described above was operated for 10 consecutive days under the same conditions as the Example 1. Upon lapse of 10 days, the column was disassembled for checking the inside of the column. As a result of checking, it was found that polymer were adhered on the welded portion of the inner wall surface of the column main body which was joined with the ladder support, and the welded portion of the inner wall surface (gas-phase contact area) of the column main body which was joined with the platform support. Further, a popcorn polymer and a viscous polymer were generated during the distillation and, thus, a sufficient polymerization suppressive effect was not obtained. Furthermore, the more the running days, the lower the purification efficiency became.

In the above arrangement, in the purification apparatus mounted with the directly-attached attachment such as a support on the outer wall thereof, lowering of the interior temperature of the apparatus due to the existence of the attachment is suppressed, thereby effectively preventing adhesion of polymer on the apparatus inner wall. Particularly, this invention is effective in suppressing adhesion of polymer on the portion of the apparatus inner wall corresponding to the site where the attachment is provided.

Accordingly, the present invention can provide an improved arrangement that prevents adhesion of polymer on or around the inner wall of a purification apparatus directly equipped on the outer wall thereof with an attachment such as a support by suppressing local temperature lowering inside the apparatus due to the existence of the attachment.

This application is based on patent application No. 2001-304051 filed in Japan, the contents of which are hereby incorporated by references.

As this invention may be embodied in several forms without departing from the spirit of essential characteristics thereof, the present embodiment is therefore illustrative and not restrictive. The scope of the invention is defined by the appended claims rather than by the description preceding them, and all changes that fall within metes and bounds of the claims, or equivalence of such metes and bounds are therefore intended to be embraced by the claims.

What is claimed is:

1. A purification apparatus comprising:
   a vessel;
   an attachment directly mounted on an outer surface of said vessel;
   a covering material made of a low heat conductive material, said covering material at least partly covering said outer surface of said vessel, and at least partly covering said attachment; and
   a mounted member mounted on said attachment with a low heat conductive member arranged between said mounted member and said attachment, at least a portion of an outer surface of said mounted member and an outer surface of said attachment including a connected portion connecting said attachment and said mounted member being covered with said covering material;
   wherein said vessel comprises a distillation column.

2. The apparatus of claim 1, wherein said purification apparatus is operable to produce an easily-polymerizable compound.

3. A purification apparatus comprising:
   a vessel;
   an attachment directly mounted on an outer surface of said vessel;
   a covering material made of a low heat conductive material, said covering material at least partly covering said outer surface of said vessel, and at least partly covering said attachment; and
   a mounted member mounted on said attachment with a low heat conductive member arranged between said mounted member and said attachment, at least a portion of an outer surface of said mounted member and an outer surface of said attachment including a connected portion connecting said attachment and said mounted member being covered with said covering material;
   wherein said mounted member is selected from a group consisting of a ladder, a lug, and a platform.

4. The apparatus of claim 3, wherein said purification apparatus is operable to produce an easily-polymerizable compound.

5. A purification apparatus comprising:
   a vessel;
   an attachment directly mounted on an outer surface of said vessel;
   a covering material made of a low heat conductive material, said covering material at least partly covering said outer surface of said vessel, and at least partly covering said attachment; and
   a mounted member mounted on said attachment with a low heat conductive member arranged between said mounted member and said attachment, at least a portion of an outer surface of said mounted member and an outer surface of said attachment including a connected portion connecting said attachment and said mounted member being covered with said covering material;

wherein said low heat conductive member is selected from a group consisting of a sheet and a gasket.

6. The apparatus of claim 5, wherein said purification apparatus is operable to produce an easily-polymerizable compound.

7. A purification apparatus comprising:
a vessel;
an attachment directly mounted on an outer surface of said vessel;
a covering material made of a low heat conductive material, said covering material at least partly covering said outer surface of said vessel, and at least partly covering said attachment; and
a mounted member mounted on said attachment with a low heat conductive member arranged between said mounted member and said attachment, at least a portion of an outer surface of said mounted member and an outer surface of said attachment including a connected portion connecting said attachment and said mounted member being covered with said covering material;
wherein said attachment is selected from a group consisting of a platform support, a ladder support, a lifting lug, and a davit.

8. The apparatus of claim 7, wherein said purification apparatus is operable to produce an easily-polymerizable compound.

9. A purification apparatus comprising:
a vessel;
an attachment directly mounted on an outer surface of said vessel;
a covering material made of a low heat conductive material, said covering material at least partly covering said outer surface of said vessel, and at least partly covering said attachment;
a plurality of attachments, each of said attachments is selected from a group consisting of a platform support, a ladder support, a lifting lug, and a davit; and
a plurality of mounted members, each of said mounted members being mounted on a respective one of said attachments with a low heat conductive member arranged therebetween;
wherein said vessel comprises a distillation column.

10. The apparatus of claim 9, wherein said purification apparatus is operable to produce an easily-polymerizable compound.

11. A purification apparatus comprising:
a vessel;
an attachment directly mounted on an outer surface of said vessel;
a covering material made of a low heat conductive material, said covering material at least partly covering said outer surface of said vessel, and at least partly covering said attachment;
a plurality of attachments, each of said attachments is selected from a group consisting of a platform support, a ladder support, a lifting lug, and a davit; and
a plurality of mounted members, each of said mounted members being mounted on a respective one of said attachments with a low heat conductive member arranged therebetween;
wherein each of said mounted members is selected from a group consisting of a ladder, a lug, and a platform.

12. The apparatus of claim 11, wherein said purification apparatus is operable to produce an easily-polymerizable compound.

13. A purification apparatus comprising:
a vessel;
an attachment directly mounted on an outer surface of said vessel;
a covering material made of a low heat conductive material, said covering material at least partly covering said outer surface of said vessel, and at least partly covering said attachment; and
a mounted member mounted on said attachment with a low heat conductive member arranged between said mounted member and said attachment, at least a portion of an outer surface of said mounted member and an outer surface of said attachment including a connected portion connecting said attachment and said mounted member being covered with said covering material;
wherein only said covering material at least partly covers said outer surface of said vessel, and at least partly covers said attachment, so that said outer surface of said vessel and said attachment are free of any heating devices.

14. The apparatus of claim 13, wherein said purification apparatus is operable to produce an easily-polymerizable compound.

15. A purification apparatus comprising:
a vessel;
an attachment directly mounted on an outer surface of said vessel;
a covering material made of a low heat conductive material, said covering material at least partly covering said outer surface of said vessel, and at least partly covering said attachment;
a plurality of attachments, each of said attachments is selected from a group consisting of a platform support, a ladder support, a lifting lug, and a davit; and
a plurality of mounted members, each of said mounted members being mounted on a respective one of said attachments with a low heat conductive member arranged therebetween;
wherein said low heat conductive member is selected from a group consisting of a sheet and a gasket.

16. A purification apparatus comprising:
a vessel;
an attachment directly mounted on an outer surface of said vessel;
a covering material made of a low heat conductive material, said covering material at least partly covering said outer surface of said vessel, and at least partly covering said attachment;
a plurality of attachments, each of said attachments is selected from a group consisting of a platform support, a ladder support, a lifting lug, and a davit; and
a plurality of mounted members, each of said mounted members being mounted on a respective one of said attachments with a low heat conductive member arranged therebetween;
wherein only said covering material at least partly covers said outer surface of said vessel, and at least partly covers said attachment, so that said outer surface of said vessel and said attachment are free of any heating devices.

* * * * *